Figure 2:
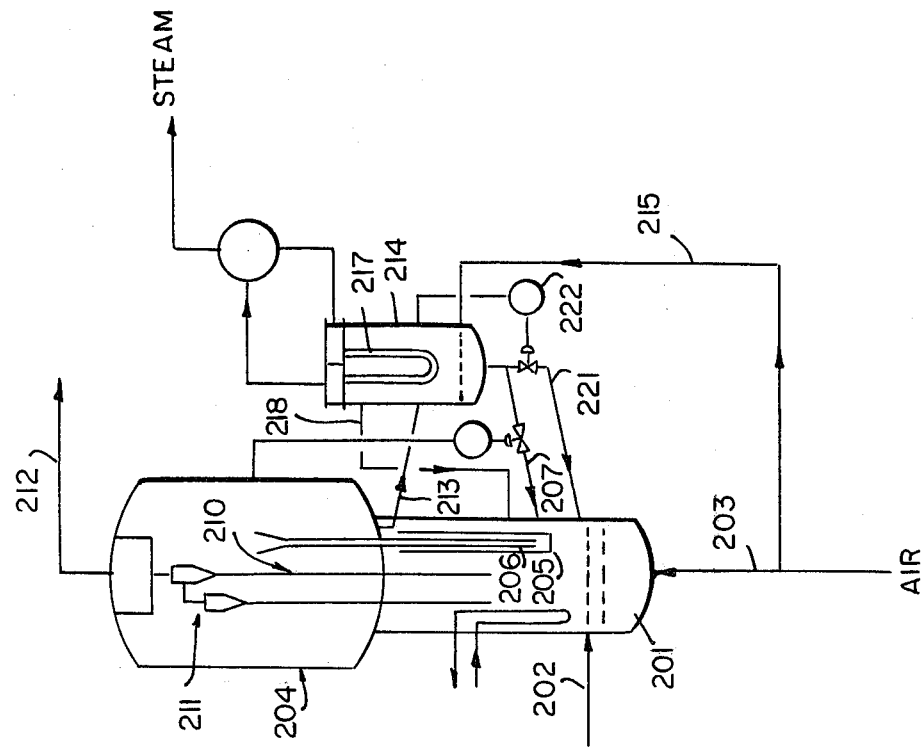

United States Patent [19]

Tsao

[11] 4,391,880
[45] * Jul. 5, 1983

[54] RECOVERY OF HEAT AND VAPORIZED MATERIAL FROM A REACTION EFFLUENT

[75] Inventor: Utah Tsao, Jersey City, N.J.

[73] Assignee: The Lummus Company, Bloomfield, N.J.

[*] Notice: The portion of the term of this patent subsequent to Jan. 6, 1998, has been disclaimed.

[21] Appl. No.: 222,081

[22] Filed: Jan. 2, 1981

Related U.S. Application Data

[63] Continuation-in-part of Ser. No. 48,147, Jun. 13, 1979, Pat. No. 4,243,650, which is a continuation-in-part of Ser. No. 870,351, Jan. 18, 1978, abandoned, and a continuation-in-part of Ser. No. 25,278, Mar. 29, 1979, abandoned.

[51] Int. Cl.$^3$ .................. B01D 5/00; C07C 120/14
[52] U.S. Cl. ..................... 423/659; 423/DIG. 13; 252/411 R; 260/465.3; 260/465.9; 562/534; 570/224; 570/243; 549/247; 549/262
[58] Field of Search ............. 423/659, DIG. 13; 260/465.3, 465.9, 346.75; 562/534; 55/69, 72; 585/902, 460, 744; 252/411 R, 465; 570/224, 243

[56] References Cited

U.S. PATENT DOCUMENTS

| | | | |
|---|---|---|---|
| 2,367,263 | 1/1945 | Brown | 252/465 X |
| 2,376,190 | 5/1945 | Roetheli et al. | 423/659 H |
| 2,407,828 | 9/1946 | Gorin | 570/241 X |
| 2,447,323 | 8/1948 | Fontana | 570/241 X |
| 2,498,546 | 2/1950 | Gorin | 570/241 |
| 2,498,552 | 2/1950 | Kilgren et al. | 570/241 X |
| 2,580,635 | 1/1952 | Winter, Jr. | 55/72 X |
| 2,701,179 | 2/1955 | McKinney | 423/74 |
| 2,897,918 | 8/1959 | Schlotthauer et al. | 55/72 X |
| 3,443,360 | 5/1969 | Reeves | 55/71 |
| 4,029,636 | 6/1977 | Lowry et al. | 260/465.3 X |
| 4,120,668 | 10/1978 | Fraley | 423/210.5 X |
| 4,243,650 | 1/1981 | Tsao | 423/210.5 |

Primary Examiner—Earl C. Thomas

[57] ABSTRACT

Process and system for cooling a reaction effluent containing volatized catalyst wherein the effluent is contacted with circulating cooled solid catalyst in dilute phase transport contact, with the volatized catalyst being condensed onto the solid catalyst.

4 Claims, 2 Drawing Figures

RECOVERY OF HEAT AND VAPORIZED MATERIAL FROM A REACTION EFFLUENT

This application is a continuation in part of U.S. Application Ser. No. 48,147, filed on June 13, 1979 now U.S. Pat. No. 4,243,650, which aforesaid application is a continuation in part of U.S. Application Ser. No. 870,351, filed on Jan. 18, 1978, now abandoned, and a continuation in part of U.S. Application Ser. No. 25,278, filed on Mar. 29, 1979, now abandoned.

This invention relates to recovery of heat and vaporized material from a reaction effluent which contains such vaporized material.

In many processes, the reaction effluent withdrawn from a reaction zone includes a vaporized material, which is derived from the use of such material in the reaction zone. In attempting to cool such effluents, such vaporized material condenses on heat exchange surfaces, thereby causing fouling thereof. In addition, in many cases, as a result of the high temperature and the presence of oxygen there is an "after-burning" problem.

Thus, for example, reaction effluent withdrawn from an ammoxidation process for producing a nitrile, by use of supported oxide catalyst, may include vaporized or volatized portions of such catalyst. There is a need for a new and improved process for effectively cooling such reaction effluent.

In accordance with the present invention, there is provided a process system for cooling a reaction effluent including volatized catalyst withdrawn from a reaction system employing the catalyst wherein the reaction effluent, containing the vaporized catalyst is contacted with the catalyst, in solid form, with such solid catalyst particles being at a temperature at which the volatized catalyst is condensed from the effluent onto the solid catalyst particles to thereby separate the volatized catalyst from the stream. Such contacting results in a cooling of the effluent and a heating of the solids, with heat subsequently being recovered from the solids by indirect heat transfer.

More particularly, the gaseous effluent, which contains the volatized catalyst, is contacted with solid catalyst particles by suspending the solid catalyst particles in the flowing gaseous reaction effluent to provide for dilute phase transport contact, with the solid particles being at a temperature at which the vaporized catalyst condenses from the gas onto the solid catalyst particles, with the solid catalyst particles being heated and the gaseous reaction effluent being cooled by such contact. The solid particles are separated from the reaction effluent, and cooled in a fluidized bed to a temperature at which the particles can be employed for cooling the reaction effluent and condensing vaporized catalyst therefrom. The cooled particles are then employed for such contacting.

In general, the fluidized bed of solid particles is provided by a fluidizing gas which is a gas to be employed as a feed in the reaction system.

Heat is recovered in the fluidized bed by cooling the particles in the bed by indirect heat transfer with a suitable heat transfer fluid, such as water, to thereby effectively recover a portion of the heat from the gaseous reaction effluent; for example, by generation of steam.

The reaction system may be operated in a manner such that a portion of the solid catalyst is maintained in the vapor space of the reactor to act as a heat sink to prevent "after-burning" of the effluent. As a result, the effluent also includes some hot solid catalyst from the reaction zone, and such hot catalyst is separated from the effluent along with the catalyst added to the effluent for cooling thereof, as hereinabove described. Such catalyst is returned to the reaction system and the rate at which catalyst is returned to the reaction system controls the level of the fluidized bed employed for cooling catalyst particles to thereby regulate the temperature of the fluidized bed.

Figure 1:
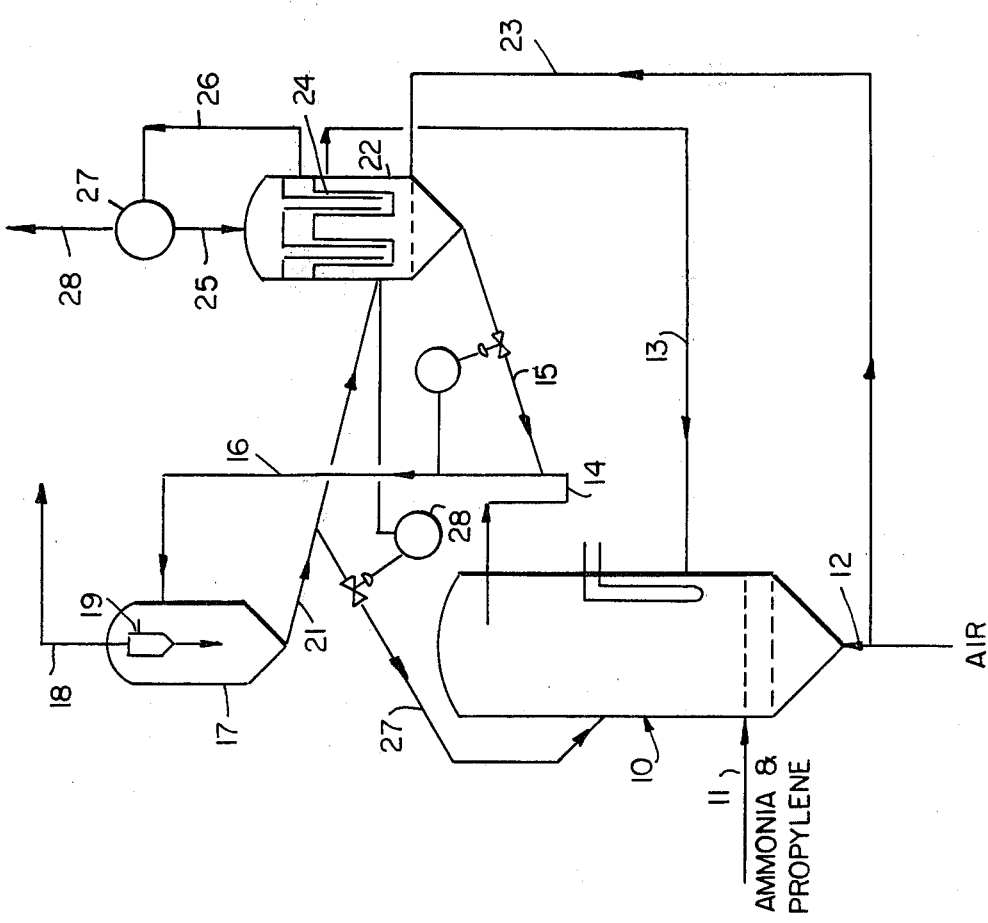

The present invention will be further described with respect to the drawings, which illustrate preferred embodiments thereof, wherein:

FIG. 1 is a simplified schematic flow diagram of one embodiment of the present invention; and FIG. 2 is a simplified schematic flow diagram of a modified embodiment.

Referring now to FIG. 1 of the drawings, there is shown a reaction system, comprised of a reactor, schematically generally indicated as 10. As particularly described, the reaction system is directed to the production of a nitrile by reaction of hydrocarbon, ammonia and air, and in particular to the production of acrylonitrile by reaction of propylene, ammonia and air. It is to be understood, however, that the teachings are equally applicable to other reaction system.

As particularly shown, the reactor 10 is provided with ammonia and propylene through line 11, fresh air feed through line 12, and further fresh air feed, obtained as hereinafter described, which is introduced into reactor 10 through line 13. The reactor 10 includes a suitable supported metal oxide catalyst for catalizing the reaction for production of acrylonitrile.

A gaseous reaction effluent, which includes a small amount of vaporized catalyst, and some solid catalyst, is withdrawn from reactor 10 through line 14, and such effluent is contacted with cooled solid catalyst particles introduced through line 15, which particles are at a temperature at which vaporized catalyst present in the gaseous effluent is condensed onto the solid catalyst particles. The inlet of line 14 should be located near the top of reactor 10 and the level of catalyst in the reactor should be maintained at a such height that the vapor space in the reactor will hold sufficient solid catalyst to prevent after-burning. The solid catalyst particles and gaseous effluent flow through line 16 in a direct contact relationship, with line 16 functioning as a dilute phase transport contactor to effect cooling of the effluent and condensation of vaporized catalyst onto the solid catalyst particles.

The mixture of gaseous effluent and solid particles, in line 16, is introduced into a gas-solid separator 17 to effect separation of the solid catalyst particles having condensed catalyst thereon from the gaseous effluent.

Gaseous effluent, essentially free of volatized catalyst, is withdrawn from separator 17 through line 18, which includes a suitable cyclone separator to maintain the gaseous effluent in line 18 essentially free of solid particles.

As should be apparent, the gaseous effluent withdrawn through line 18 has been effectively cooled by the direct contact with the solid catalyst particles, with the solid catalyst particles having been heated as a result of such contact. The effluent is further treated (not shown) to recover product therefrom. As the effluent is free of volatized catalyst the fouling caused by the condensation of the volatized catalyst on the indirect heat transfer surface in the effluent treatment system is effectively eliminated.

The solid catalyst particles, having condensed catalyst thereon, are withdrawn from separator 17 through line 21 and introduced into a heat recovery vessel, schematically generally indicated as 22. In vessel 22, heat is recovered from the solid catalyst particles by indirectly cooling the solid particles in vessel 22 as a fluidized bed. The particles are maintained in a fluidized state by a fluidizing gas introduced through line 23, with such fluidizing gas being a portion of the feed to the reaction system. In particular, as shown, the fluidizing gas is a portion of the air feed to reactor 10. It is to be understood, however, that other portions of the feed could also be employed. The fluidized bed of solid particles in vessel 22 is cooled to a temperature at which the solid catalyst particles can condense vaporized catalyst from the gaseous effluent in line 14. For this purpose, the bed is provided with a cooling coil, schematically generally indicated as 24, which is provided with a heat transfer fluid, such as water. More particularly, water is introduced into the inlet portion of the cooling device through line 25, and as a result of the indirect heat transfer with the fluidized bed of solid catalyst, steam is generated from such water. A steam-water mixture is withdrawn from the cooling device 24 through line 26 and introduced into a vapor-liquid separation tank, schematically generally indicated as 27. Steam is withdrawn from tank 27 through line 28, with water being withdrawn therefrom through line 25. Make-up water may be introduced into the tank (not shown). In this manner, heat recovered from the gaseous effluent by the solid particles is recovered, with such recovery, as particularly described, being utilized for the generation of steam.

The fluidizing gas introduced through line 23 is heated by the solid particles. Such heated gas is withdrawn from vessel 22 through line 13 for introduction into reactor 10. As should be apparent, in this manner, a portion of the feed gas to reactor 10 is preheated by direct contact with the solid catalyst particles in vessel 22.

As particularly shown, solid catalyst particles may be returned to reactor 10 through line 27, which includes a suitable valve for controlling such catalyst return, which is operated in response to a level controller, schematically generally indicated as 28, responsive to the level of solid catalyst in vessel 22.

The level of catalyst in vessel 22 controls the temperature of the bed; accordingly, catalyst is returned through line 27 to maintain a certain bed level and thereby a certain bed temperature.

As hereinabove noted, as a result of maintaining some catalyst in the vapor space to function as a heat sink to reduce the possibility of combustion in reactor 10, the effluent includes solid as well as volatized catalyst. Such catalyst is returned to reactor 10 and a portion thereof can be employed to provide additional catalyst for the cooling system to either maintain or increase the level of the fluidized bed in vessel 22.

As should be apparent, volatized catalyst condensed onto the solid catalyst particles would also be returned to the reaction system.

A modification of the embodiment of FIG. 1 is shown in FIG. 2 of the drawings. In accordance with the modified embodiment of FIG. 2, the dilute phase transport contact line has been moved into the interior of the reaction vessel, and the gas-solid separator has been integrated with the reactor.

Referring to FIG. 2 of the drawings, there is shown a reactor 201 which is provided with propylene and ammonia through line 202, and a portion of the fresh air feed through line 203.

The top portion of the reactor 201 has integrated therewith a gas-solid separation vessel 204, with communication between the vessels being as hereinafter described.

Gaseous effluent, including volatized catalyst, is withdrawn from reactor 201 through overflow tube 205, having an internal lift tube 206, with such lift tube 206 having an outlet within the interior of separation vessel 204. As described with respect to the embodiment of FIG. 1, the top of the overflow tube 205 should be at such a height that the vapor space in the reactor will hold sufficient solid catalyst to prevent after-burning. Accordingly, the withdrawn effluent also generally includes some solid catalyst.

Cooled solid catalyst, which is at a temperature at which vaporized catalyst present in the gaseous effluent is condensed onto the solid catalyst particles is introduced into the bottom portion of the lift tube 206 through line 207, with the lift tube functioning as a dilute phase transport contact zone to provide a direct contact heat exchange relationship between the solid catalyst and flowing gaseous effluent. As a result of the direct contact cooling of the gaseous effluent, vaporized catalyst is condensed onto the solid catalyst particles. In addition, the effluent is cooled, and the solid catalyst particles are heated.

The mixture flows out of the lift tube 206 into the separation vessel 204 to effect separation of solid catalyst particles having condensed catalyst thereon from the gaseous effluent.

The gaseous effluent is withdrawn from separator 204 through a pair of cyclone separators, generally designated as 211, which are in series with each other, and which have solids withdrawing dip legs, generally designated as 210, extending into the reactor 201 for returning to reactor 201, any solid catalyst still present in the effluent. The reaction effluent is withdrawn through line 212 for further treatment. As the effluent is free of volatized catalyst the fouling caused by the condensation of the volatized catalyst on the indirect heat transfer surface in the effluent treatment system is effectively eliminated.

Solid catalyst particles, having condensed catalyst thereon are withdrawn from separator 204 through line 213, and introduced into a cooling vessel 214 for reducing the temperature of the catalyst particles. As hereinabove described with respect to the embodiment of FIG. 1, the catalyst particles are maintained as a fluidized bed in vessel 214 by introduction of a portion of the air feed for reactor 201, with such portion being introduced into vessel 214 through line 215, as a fluidizing gas. The temperature of the bed in vessel 214 is regulated by indirect heat transfer by water, which is converted to steam, flowing through suitable coils 217.

Cooled catalyst particles are withdrawn from vessel 214 through line 207 for use in cooling the reaction effluent.

Heated air, which was employed as a fluidizing gas in vessel 214 is withdrawn therefrom through line 218 for introduction into the reactor 201.

Catalyst may be returned to reactor 201 through line 221 which includes a suitable valve for controlling flow therethrough. As described with respect to the embodiment of FIG. 1, the valve in line 221 may be operated by a suitable level control device, schematically generally indicated as 222, which is responsive to the level of catalyst particles in vessel 214.

In accordance with the embodiment of FIG. 2, there is provided an integrated separator and reactor which reduces overall height. In addition, the lift tube is within the reactor which eliminates the necessity for outside piping which would require expansion joints, insulation, etc.

Although the present invention has been particularly described with respect to a reaction system for producing nitrile, the present invention is equally applicable to other systems in which the reaction effluent includes volatized catalyst derived from catalytic systems employing catalysts with a low vapor pressure, and wherein it is required to cool such effluent. Thus, for example, the invention is applicable to processes directed to the production of:

(1) oxychlorination (to produce EDC)
(2) phthalic anhydride
(3) maleic anhydride
(4) acrylic acid
(5) acrolein The present invention is advantageous in that it provides effective cooling of the effluent, while preventing fouling which would be caused by the presence of volatized catalyst; i.e., condensation of catalyst on indirect heat transfer surfaces, is effectively eliminated.

These and other advantages should be apparent to those skilled in the art from the teachings herein.

Numerous modifications and variations of the present invention are possible in light of the above teachings, and therefore, within the scope of the appended claims, the invention may be practised otherwise than as particularly described.

I claim:

1. A process for cooling a gaseous reaction effluent containing volatized catalyst and withdrawn from a reaction system employing a solid catalyst, comprising:
   contacting the gaseous reaction effluent with solid catalyst particles by suspending the solid catalyst particles in flowing gaseous reaction effluent to provide dilute phase transport contact, said solid catalyst particles being at a temperature at which vaporized catalyst condenses from the gas onto the solid catalyst particles, said solid catalyst particles being heated and said gaseous reaction effluent being cooled by said contact;
   separating gaseous reaction effluent from the solid catalyst particles;
   cooling separated solid catalyst particles in a fluidized bed, said fluidized bed being fluidized by a fluidizing gas, said particles being cooled in the fluidized bed to a temperature at which vaporized salt condenses onto the solid particles, said fluidizing gas being a feed gas to the reaction system and being introduced into the reaction system subsequent to use thereof as the fluidizing gas; and
   employing cooled solid catalyst particles for contacting the gaseous reaction effluent.

2. The process of claim 1 wherein the solid catalyst particles are cooled in the fluidized bed by indirect heat transfer.

3. The process of claim 2 wherein the reaction system is a system for producing a nitrile.

4. The process of claim 1 wherein the gaseous reaction effluent includes solid catalyst particles and a portion of the separated solid catalyst particles are returned to the reaction system to maintain a level of solid catalyst particles in the fluidized bed.

* * * * *